(12) United States Patent
Oh

(10) Patent No.: US 8,491,885 B2
(45) Date of Patent: Jul. 23, 2013

(54) METHOD FOR PROMOTING THE SELF-RENEWAL OF ADULT STEM CELLS USING MESENCHYMAL STROMAL CELLS

(75) Inventor: Il Hoan Oh, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 346 days.

(21) Appl. No.: 12/668,540

(22) PCT Filed: Jul. 16, 2008

(86) PCT No.: PCT/KR2008/004175
§ 371 (c)(1),
(2), (4) Date: Apr. 26, 2010

(87) PCT Pub. No.: WO2009/011546
PCT Pub. Date: Jan. 22, 2009

(65) Prior Publication Data
US 2010/0297089 A1    Nov. 25, 2010

(30) Foreign Application Priority Data
Jul. 16, 2007    (KR) ........................ 10-2007-0071098

(51) Int. Cl.
*A01N 63/00* (2006.01)
*A61K 48/00* (2006.01)
*C12N 5/00* (2006.01)
*C12N 5/02* (2006.01)

(52) U.S. Cl.
USPC ......... 424/93.21; 435/325; 435/373; 435/377

(58) Field of Classification Search
USPC ........................ 424/93.21; 435/325, 373, 377
See application file for complete search history.

(56) References Cited

U.S. PATENT DOCUMENTS
6,465,249 B2    10/2002    Reya et al.

OTHER PUBLICATIONS

Mimeault et al. Clinical Pharmacology & Therapeutics: 82(3): 252-264, 2007.*
Jing et al. Haemalogica, 95: 542-550, 2010.*
The Sigma-Aldrich catalog (http://www.sigmaaldrich.com/catalog/, accessed online on Jun. 4, 2010, "neural stem cells" and "Stemline Neural Stem cell Expansion Medium".*
D'Souza et al., Oncogene, 27: 5148-5167, 2008.*
Benedito et al., Cell, 137: 1124-1135, 2009.*
Adipogen, Notch Ligands, Product Flyer, pp. 1-6, 2010.*
Waskow et al., Nature, 6(4): 267-269, 2009.*
Chiba, H. et al., "Wnt3 modulates the characteristics and cobblestone area-supporting activity of human stromal cells," Experimental Hematology, 2004, vol. 32, pp. 1194-1203.
Jones, P. et al., "Stromal Expression of Jagged 1 Promotes Colony Formation by Fetal Hematopoietic Progenitor Cells," Blood, Sep. 1, 1998, vol. 92, No. 5, pp. 1505-1511.
Reya, T. et al., "A role for Wnt signaling in self-renewal of haematopioetic stem cells," Nature, May 22, 2003, vol. 423, pp. 409-414.
Bonnet, D., Birth Defects Research (Part C) 69: 219-229 (2003).
Fumio, A. et al., Blood (ASH Annual Meeting Abstracts) American Society of Hematology 104: Abstract 669 (2004).
Israsena, N. et al., Developmental Biology 268: 220-231 (2004).
KIPO Office Action for Korean Application No. 10-2008-0069323 (Sep. 28, 2010).

* cited by examiner

*Primary Examiner* — Thaian N Ton
(74) *Attorney, Agent, or Firm* — Don J. Pelto, Esquire; Sheppard, Mullin, Richter & Hampton LLP

(57) ABSTRACT

The present invention relates to a composition for promoting the self-renewal of adult stem cells, comprising β-catenin or notch ligand-overexpressed mesenchymal stromal cells. Further, the present invention relates to a method for promoting the self-renewal of adult stem cells by co-culturing adult stem cells with the mesenchymal stromal cells. Furthermore, the present invention relates to β-catenin or notch ligand-overexpressed mesenchymal stromal cells for promoting the self-renewal of adult stem cells.

6 Claims, 11 Drawing Sheets

A

Control-CM | Wnt3a-CM

Jagged-1

B

Control-CM | Wnt3a-CM

Dll-1

No. of Nestin+ cells in the co-culture of neural stem cells

METHOD FOR PROMOTING THE SELF-RENEWAL OF ADULT STEM CELLS USING MESENCHYMAL STROMAL CELLS

This application is a National Stage entry of International Application No. PCT/KR08/04175, filed Jul. 16, 2008, which claims priority to Korean application 10-2007-0071098, filed Jul. 16, 2007.

TECHNICAL FIELD

The present invention relates to a composition for promoting the self-renewal of adult stem cells, comprising β-catenin or notch ligand-overexpressed mesenchymal stromal cells. Further, the present invention relates to a method for promoting the self-renewal of adult stem cells by co-culturing adult stem cells with the mesenchymal stromal cells. Furthermore, the present invention relates to β-catenin or notch ligand-overexpressed mesenchymal stromal cells for promoting the self-renewal of adult stem cells.

BACKGROUND ART

Adult stem cell defines a stem cell found in a differentiated tissue in an adult organism which may, with certain limitations, differentiate to yield all the specialized cell types of the various tissues. Adult stem cells may be derived from cells of the group consisting of breast, bone marrow, umbilical cord blood, peripheral blood, liver, skin, gastrointestinal tract, placenta, and uterus. Adult stem cells include neuronal stem cells capable of differentiating into neuronal cells, hematopoietic stem cells capable of differentiating into blood cells, mesenchymal stem cells capable of differentiating into bone, cartilage, fat, and muscle, and hepatic stem cells capable of differentiating into hepatocytes.

Among them, hematopoietic stem cells (HSCs) constitute a rare subpopulation in hematopoietic tissues with the ability to give rise to all types of mature blood cells. These hematopoietic stem cells exhibit long-term repopulating activities when transplanted into myeloablated hosts through their unique ability to execute self-renewal during regeneration. The cells are referred to as competitive repopulating units (CRUs), and quantitative increments in these CRU numbers have been the key evidence for self-renewal of hematopoietic stem cells.

On the other hand, Wnt proteins constitute a large family of cysteine-rich secreted ligands, which bind to membrane receptors via an autocrine or paracrine mechanism, and thus activate the Wnt pathway (receptor-mediated signal transduction pathway). In vertebrates, the Wnt signaling pathway functions to regulate organ development, and cellular proliferation, morphology, motility, and fate (Logan, C. Y., and R. Nusse. 2004. 20:781-810). The Wnt signaling pathway is divided into two branches whose differential activation depends on the binding of Wnt proteins to membrane receptors. One is the β-catenin-dependent Wnt pathway, also called canonical Wnt pathway, which is activated by Wnt1, Wnt2, Wnt3a, Wnt10a or the like, regulates cell fate determination, and is involved in cell proliferation or survival. The other is the β-catenin-independent Wnt pathway, also called non-canonical Wnt pathway or Wnt/calcium pathway, which is activated by Wnt4, Wnt5a, and Wnt11, and mediates cell polarity, adhesion, and shape.

In the canonical Wnt pathway, β-catenin is destabilized by a destruction complex composed of Axin, serine-threonine kinase, and glycogen synthase kinase 3β in the absence of Wnt signals. Wnt binding to Frizzled family receptors and LRP5/6 inhibits the formation of a destruction complex, and induces β-catenin stabilization and its entry into the nucleus where it activates TCF/LEF target genes (Wodarz, A., and R. Nusse. 1998. *Annu Rev Cell Dev Biol* 14:59-88).

There are many studies on the role of β-catenin in the self-renewal of hematopoietic stem cells. In a recent study on mice with conditional inactivation of β-catenin, normal hematopoietic development and repopulating activity were observed, suggesting that β-catenin activity is dispensable for HSC function (Cobas, M., A. et al. 2004. *J Exp Med* 199:221-229). Furthermore, mice with in vivo stabilized β-catenin exhibited defective hematopoietic repopulation and differentiation during steady-state or stimulated conditions in a myeloablated host (Kirstetter P., et al. 2006. *Nat Immunol* 7:1037-1047), which were nevertheless accompanied by expansion of phenotypically defined HSCs. Thus, the precise role of β-catenin in hematopoiesis remains unclear.

DISCLOSURE

Technical Problem

Accordingly, the present inventors have made intensive studies on the role of β-catenin in the microenvironmental regulation of adult stem cell behavior. They found that the Wnt signaling pathway primarily targets the stroma, and the activated stroma serves as a microenvironmental cue for the self-renewal of adult stem cells during steady-state, in particular, the self-renewal of hematopoietic stem cells or neuronal stem cells is promoted when they are co-cultured with β-catenin-overexpressed mesenchymal stromal cells (MSC). Furthermore, the present inventors found that the notch ligands, jagged-1, dll-1 and dlk-1 are notably overexpressed in β-catenin activated mesenchymal stromal cells to induce notch signal activation, thereby completing the present invention.

Technical Solution

It is an object of the present invention to provide a composition for promoting the self-renewal of adult stem cells, comprising β-catenin or notch ligand-overexpressed mesenchymal stromal cells.

It is another object of the present invention to provide a method for promoting the self-renewal of adult stem cells by co-culturing the adult stem cells with the β-catenin or notch ligand-overexpressed mesenchymal stromal cells.

It is still another object of the present invention to provide β-catenin-overexpressed mesenchymal stromal cells for promoting the self-renewal of adult stem cells.

(C) and (D) are comparison of engraftment levels of 5-FU BMCs that are transduced with MPG or MPG-β-catenin, (E) shows the result of measuring CRU frequencies in the transduced BMCs, and (F) shows the effect of β-catenin on differentiation of hematopoietic stem cells.

Figure 2:
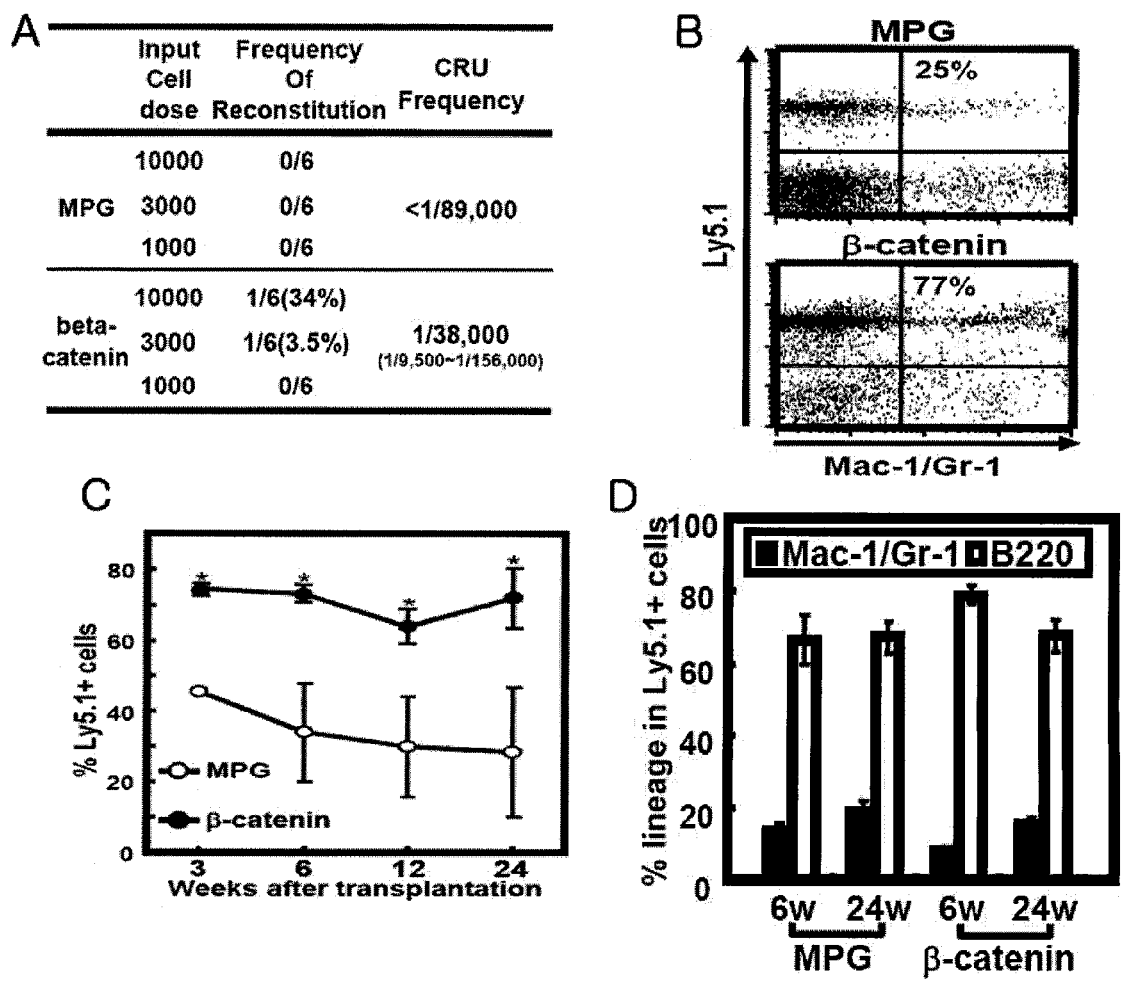

FIG. 2 shows the effect of β-catenin stabilized stromal cells on the repopulating activity of co-cultured hematopoietic stem cells;

(A) shows frequency of reconstitution and CRU frequency after transplantation of hematopoietic stem cells co-cultured with mesenchymal stromal cells that are transduced with each vector, (B) shows the engraftment levels and the myeloid (Mac-1/Gr-1 positive) and lymphoid (Mac-1/Gr-1 negative) distribution of donor-derived cells (Ly5.1), in which 5-FU BMCs were co-cultured on stromal cells transduced with MPG or MPG-β-catenin for 5 days, and then cultured cells were transplanted into lethally irradiated recipient mice (Ly5.2), (C) shows mean % donor-derived leukocytes (Ly5.1+) cells in the recipient blood at the time indicated after transplantation (n=4 for each; *: P<0.05), in which 5-FU BMCs were co-cultured on stromal cells transduced with MPG or MPG-β-catenin for 5 days, and then cultured cells were transplanted into lethally irradiated recipient mice (Ly5.2), and (D) shows the myeloid (Mac-1/Gr-1) and lymphoid (B220) lineages of donor-derived reconstituted cells in recipient blood, in which 5-FU BMCs were co-cultured on stromal cells transduced with MPG or MPG-β-catenin for 5 days, and then cultured cells were transplanted into lethally irradiated recipient mice (Ly5.2). % represents levels of donor-derived transduced (GFP+) cells.

Figure 3:
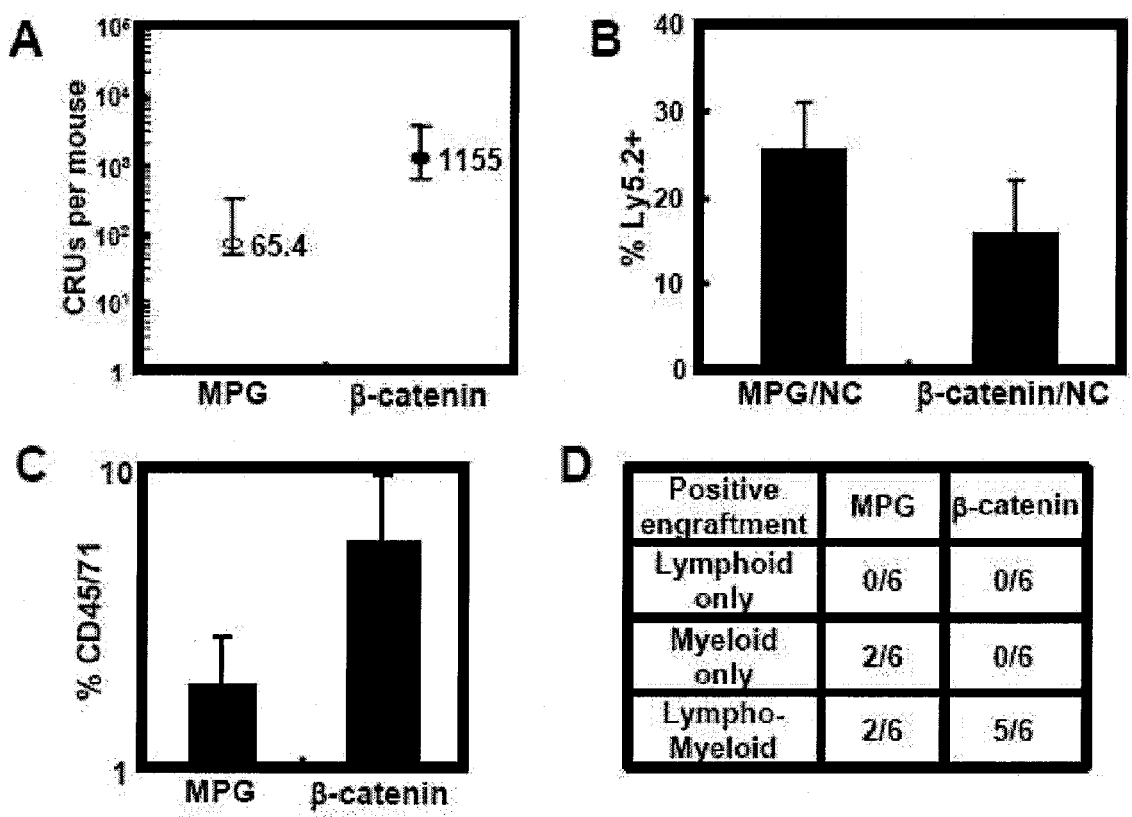

In FIG. 3, (A) shows each CRU frequency determined 16 weeks after secondary transplantation by applying Poisson statistics, in which total CRU numbers were calculated assuming that the two femurs and tibiae represent 25% of total marrow, and values are the mean for the total number of donor-derived (Ly5.1) CRUs per mouse with error bars representing the upper and lower limits of a 95% C.I (confidence interval) equivalent to ±2 SEM (±2SEM), (B) shows the effect of transwell filter separation during co-culture, (C) shows the effect of the stable form of β-catenin on expansion of human hematopoietic stem cells, and (D) shows the frequency of myeloid-lymphoid reconstituted cells after transplantation of CD34+ (limiting dose, 5×14) co-cultured on stromal cells transduced with MPG or MPG-β-catenin (n=6 for each).

Figure 4:
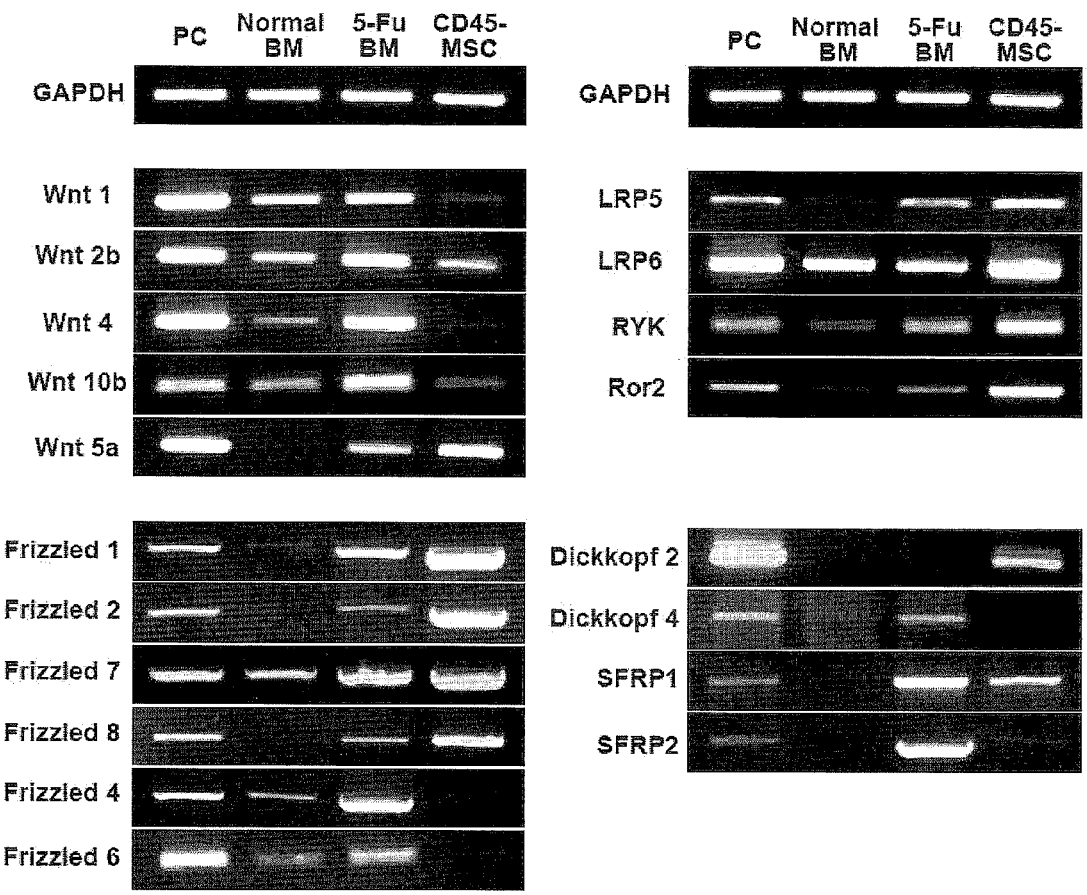

FIG. 4 is the result of RT-PCR analysis of indicated molecules in normal BM, 5-FU BMCs, and MSCs sorted for CD45(-), for analysis of compartmentalized expression pattern of Wnt-related genes in hematopoietic and stromal cells (PC: positive control).

Figure 5:
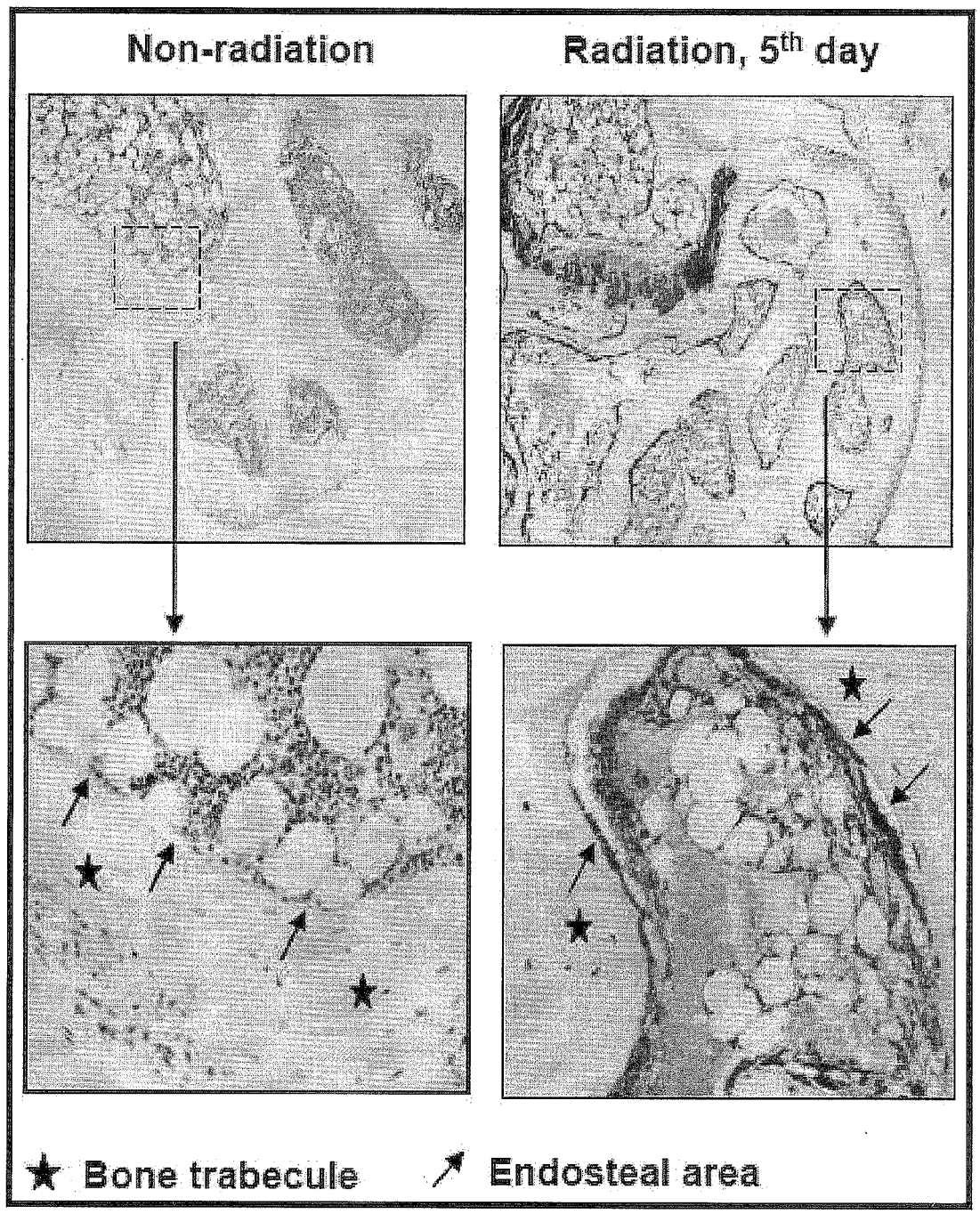

FIG. 5 shows the effect of activated β-catenin expression in bone marrow stroma including the trabecular endosteum on the self-renewal of hematopoietic stem cells, in which the active form of β-catenin accumulated selectively in the trabecular endosteum in "irradiation-stressed" but not in "steady-state" marrows.

Figure 6:
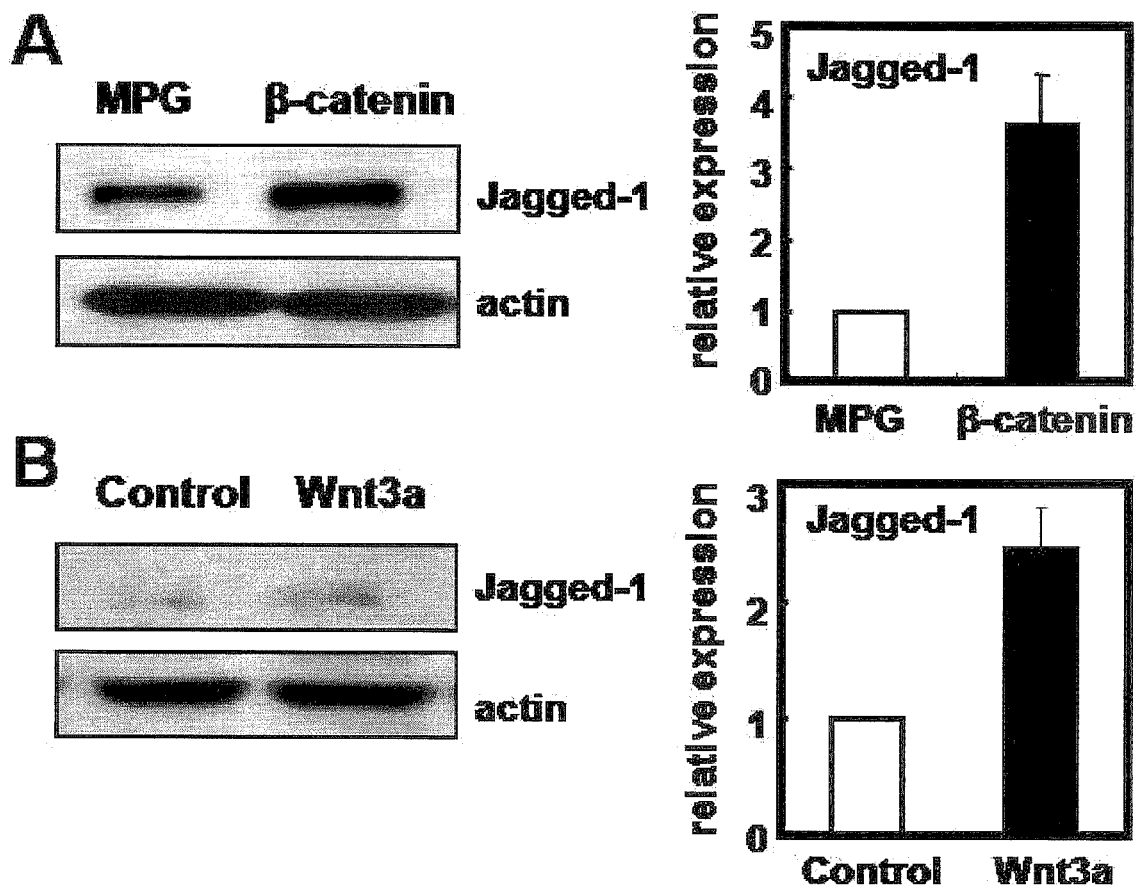
Figure 7:
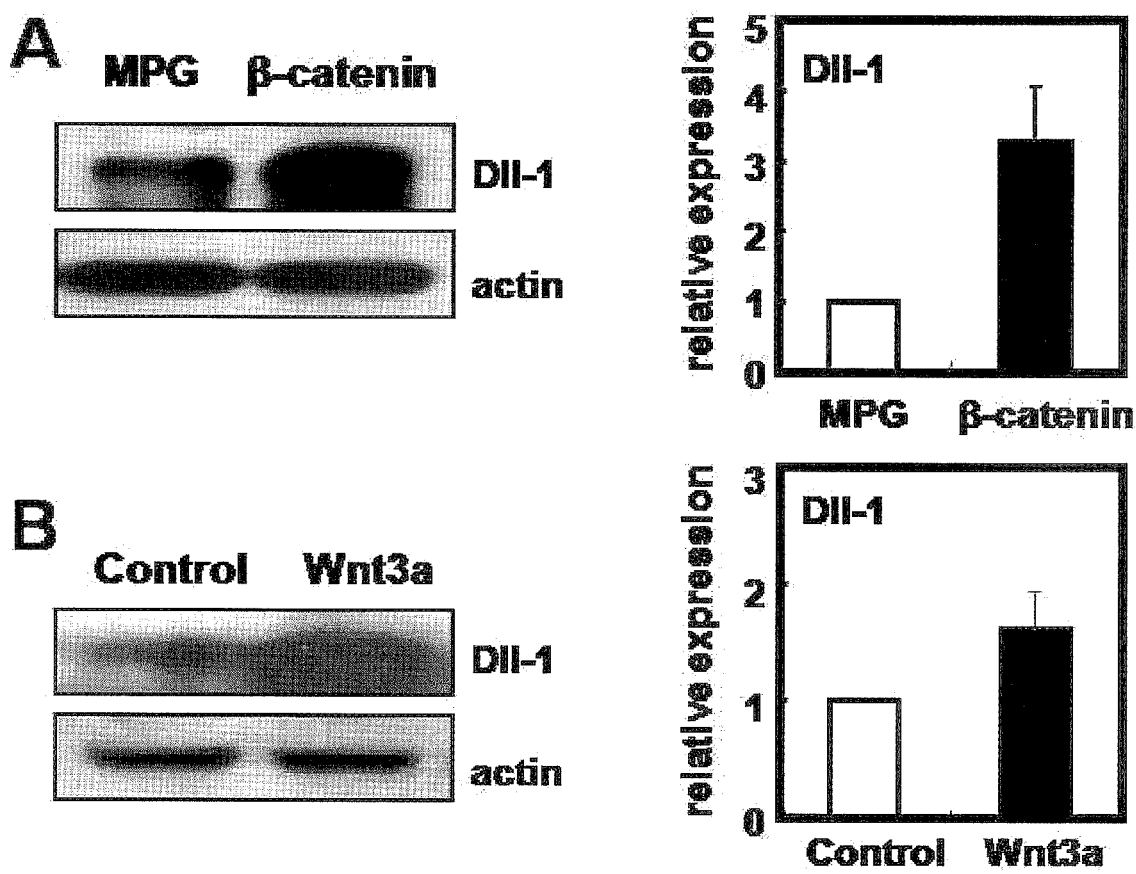
Figure 8:
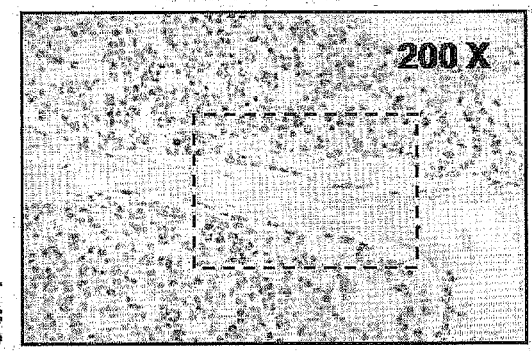
Figure 8:
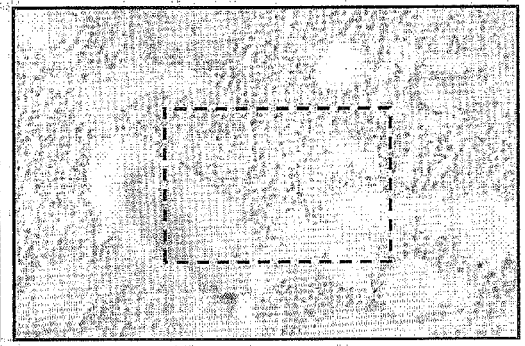
Figure 8:
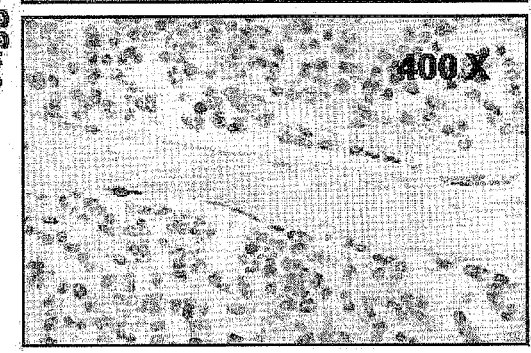
Figure 8:
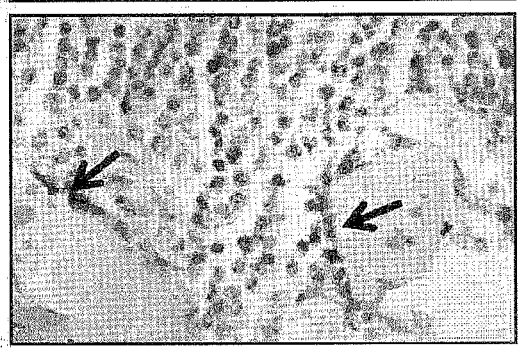
Figure 8:
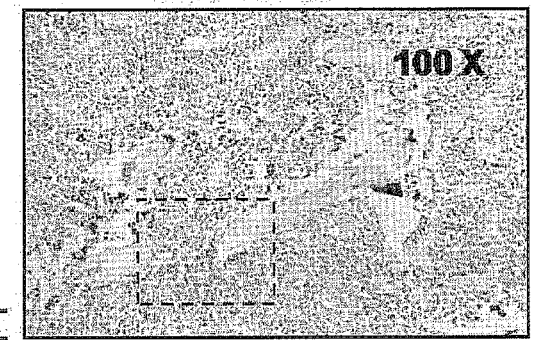
Figure 8:
Figure 8:
Figure 8:

FIGS. 6 to 8 show the induction of notch ligands in wnt/β-catenin activated mesenchymal stromal cells;

(A) in FIG. 6 is the result of Western blotting and real time PCR showing the induction of jagged-1 in β-catenin activated mesenchymal stromal cells, and (B) is the result of immunoblotting and real time PCR showing the induction of jagged-1 in mesenchymal stromal cells by stimulation with Wnt-3a CM, (A) in FIG. 7 is the result of Western blotting and real time PCR showing the induction of dll-1 in β-catenin activated mesenchymal stromal cells, and (B) is the result of immunoblotting and real time PCR showing the induction of dll-1 in mesenchymal stromal cells by stimulation with Wnt-3a CM.

FIG. 8 shows selective induction of jagged-1 (A) and dll-1 (B) in the bone marrow microenvironment of mice stimulated with Wnt 3a, in which mice were intravenously injected with Wnt3a-CM or control CM, and their bone marrows were examined 24 hrs thereafter for indicated notch ligand by immunohistochemistry. Shown are the images at indicated low and higher magnification (200× and 400×). Arrows indicate positive staining (brown color, DAB) of each antibody in the endosteum of trabecule.

Figure 9:
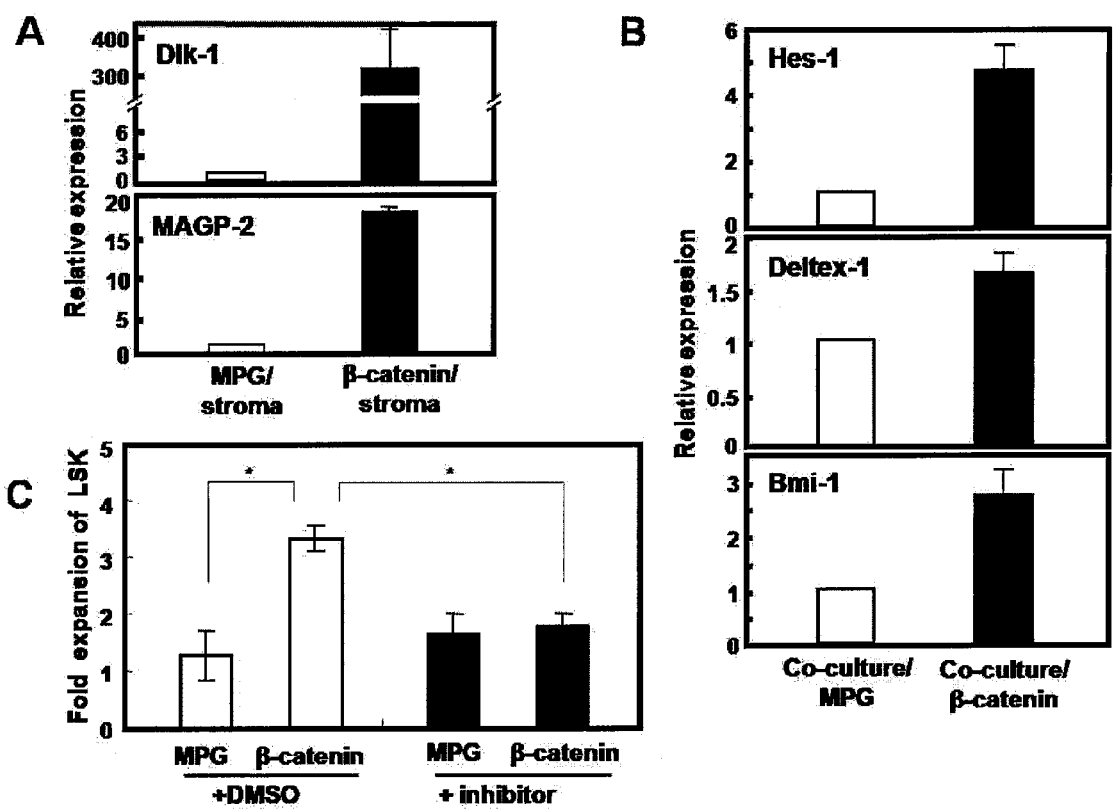

FIG. 9 shows notch signal activation in the microenvironmental cross-talk with HSC;

(A) shows Real-time PCR confirmation of the indicated notch-related genes, (B) shows activation of notch signals in co-cultured hematopoietic stem cells, and (c) shows effect of notch signal inhibitor on the co-cultured hematopoietic stem cells.

Figure 10:
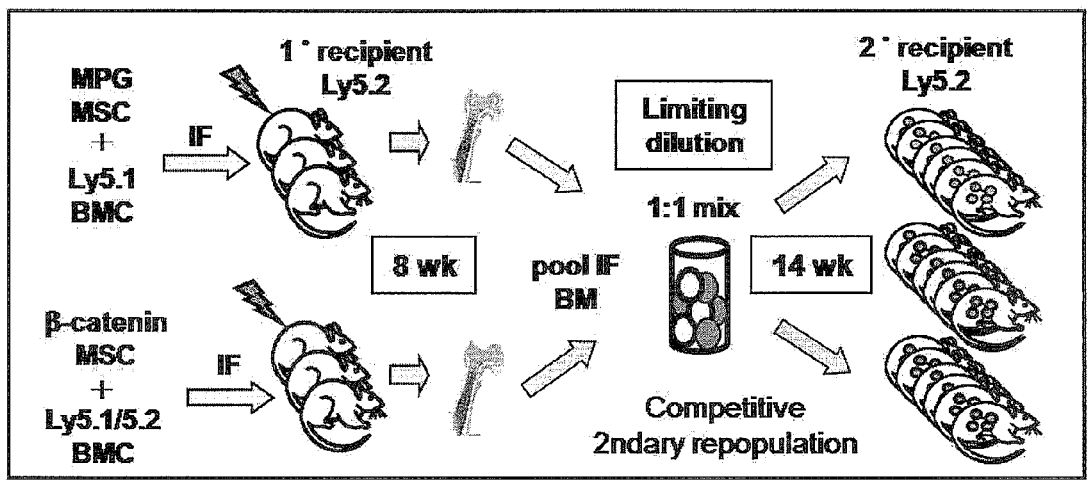

FIG. 10 shows the effect of β-catenin activated mesenchymal stromal cells on the self-renewal of HSCs in-vivo, in which the upper panel shows a schematic illustration of the experimental design, and the lower panel shows CRU frequency of each donor-origin regenerated BMCs. Shown are the CRU frequencies for each group BMCs (Ly5.1 or Ly5.1/5.2) in primary recipient mice obtained by applying Poisson statistics, and the relative CRU frequency of the regenerated BMCs was obtained by setting the frequency of the control group (Ly5.1) to 1.0.

Figure 11:
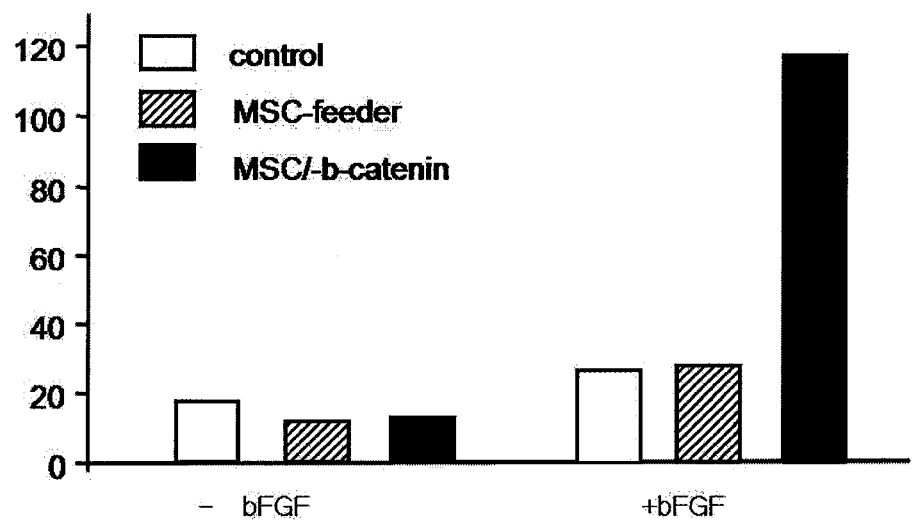

FIG. 11 shows the effect of β-catenin activated mesenchymal stromal cells on expansion of neuronal.

BEST MODE

In accordance with an aspect, the present invention relates to a composition for promoting the self-renewal of adult stem cells, comprising β-catenin or notch ligand-overexpressed mesenchymal stromal cells.

As used herein, the term "mesenchymal stromal cell (MSC)" refers to a cell that gives rise to cartilage, bone, fat, bone marrow stroma, muscle, and nerve, and is generally present in and isolated from umbilical cord blood, peripheral blood, and other tissues as well as adult bone marrow. In the present invention, the mesenchymal stromal cells encompass those derived from all animals including humans, monkeys, pigs, horses, cows, sheep, dogs, cats, mice, and rats, and preferably those derived from humans. The term "mesenchymal stromal cell" is interchangeable with "mesenchymal stem cell" or "stromal cell".

As used herein, the term "adult stem cell" refers to a stem cell found in a differentiated tissue in an adult organism and may, with certain limitations, differentiate to yield all the specialized cell types of the tissue. Adult stem cell may be derived from the group consisting of breast, bone marrow, umbilical cord blood, peripheral blood, liver, skin, gastrointestinal tract, placenta, and uterus. Adult stem cells include neuronal stem cells capable of differentiating into neuronal cells, hematopoietic stem cells capable of differentiating into blood cells, mesenchymal stem cells capable of differentiating into bone, cartilage, fat, and muscle, and hepatic stem cells capable of differentiating into hepatocytes. In the present invention, adult stem cells are preferably hematopoietic stem cells or neuronal stem cells.

As used herein, the term "hematopoietic stem cell (HSC)" refers to an undifferentiated progenitor cell that gives rise to a succession of mature functional blood cells including red blood cell, white blood cell, and platelet. As used herein, the term "neuronal stem cell (NSC)" refers to an undifferentiated stem cell that resides in the nervous system and generates neuronal cells including astrocyte, neuron, and oligodendrocyte. These hematopoietic stem cells or neuronal stem cells exhibit long-term repopulating activities when transplanted into a myeloablated or denervated host through their unique ability to execute self-renewal during regeneration. In the present invention, the adult stem cells encompass those derived from all animals including humans, monkeys, pigs, horses, cows, sheep, dogs, cats, mice, and rats, and preferably those derived from humans. In addition, the adult stem cells and mesenchymal stromal cells may be obtained by general methods that are widely known in the art.

As used herein, the term "self-renewal" is, also called self-replication or self-regeneration, one of the unique properties of stem cells, and an ability to produce daughter stem cells with the same phenotype and characteristics as the original stem cell. In particular, self-renewal, as used herein, is defined as the ability to continue proliferation while maintaining an undifferentiated state.

In the present invention, β-catenin includes a wild-type or stable form of β-catenin, and the preferred example of the stable form is β-catenin of which Ser33 is substituted with Tyr. In the present invention, β-catenin may be overexpressed in the mesenchymal stromal cells by using a known method in the art, preferably by transducing the mesenchymal stromal cell with a vector expressing β-catenin.

In the present invention, the notch ligand includes jagged-1, dll-1, and dlk-1. In the present invention, the notch ligands may be overexpressed in the mesenchymal stromal cells by using a known method in the art, preferably by transducing the mesenchymal stromal cell with a vector expressing the notch ligand.

As used herein, the term "vector", which describes an expression vector capable of expressing a protein of interest in a suitable host cell, refers to a gene construct that comprises essential regulatory elements to which a gene insert is operably linked in such a manner as to be expressed in a host cell. As used herein, the term "operably linked" refers to a functional linkage between a nucleic acid expression control sequence and a nucleic acid sequence coding for a target protein in such a manner as to allow general functions. The operable linkage to a recombinant vector may be prepared using a genetic recombinant technique well known in the art, and site-specific DNA cleavage and ligation may be easily achieved using enzymes generally known in the art. The vector includes plasmid vectors, cosmid vectors, and viral vectors, preferably viral vectors. Examples of the viral vectors include vectors derived from retrovirus such as HIV (Human immunodeficiency virus), MLV (Murine leukemia virus), ASLV (Avian sarcoma/leukosis), SNV (Spleen necrosis virus), RSV (Rous sarcoma virus), and MTV (Mouse mammary tumor virus), adenovirus, adeno-associated virus, and herpes simplex virus, but are not limited thereto. A preferred vector is a retroviral vector. In one specific embodiment of the present invention, the used vector is a retroviral vector containing a MSCV (murine stem cell virus)-derived LTR (long terminal repeat) region, a β-catenin coding region, a PGK (phosphoglycerate kinase) promoter, and a GFP (green fluorescent protein) coding region (FIG. 1A).

As used herein, the term "culture media" means media which assures the growth and survival of adult stem cells in vitro, and which may include all of the pertinent media typically used in the art. The culture media and conditions depend on the kind of stem cells. Preferable is a cell culture minimum medium (CCMM), which generally comprises a carbon source, a nitrogen source and trace elements. Examples of the CCMM include, but are not limited to, DMEM (Dulbecco's Modified Eagle's Medium), MEM (Minimal Essential Medium), BME (Basal Medium Eagle), RPMI1640, F-10, F-12, αMEM (α Minimal Essential Medium), GMEM (Glasgow's Minimal Essential Medium), and IMDM (Iscove's Modified Dulbecco's Medium). In the CCMM, an antibiotic, such as penicillin, streptomycin, and gentamicin, may be added.

The β-catenin or notch ligand-overexpressed mesenchymal stromal cells may be added to the culture media without restriction to the kind of culture media or culture type. In this regard, the β-catenin or notch ligand-overexpressed mesenchymal stromal cells may be used alone or in combination with one or more known substances promoting the self-renewal of adult stem cells.

The composition for promoting the self-renewal of hematopoietic stem cells of the present invention may be used for the treatment of patients in need of transplant, in particular, patients who suffer from acute leukemia, chronic leukemia, myelodysplastic syndrome, lymphoma, multiple myeloma, germ cell tumors, breast cancer, ovarian cancer, small cell lung cancer, solid tumors such as neuroblastoma, aplastic anemia, sickle cell anemia, Gaucher disease, Hunter syndrome, ADA deficiency, immune diseases such as Wiskott-Aldrich syndrome, metabolic diseases, and autoimmune diseases such as rheumatoid arthritis, systemic lupus erythematosus, and multiple sclerosis. In addition, the composition for promoting the self-renewal of hematopoietic stem cells of the present invention may be used to restore the hematopoietic cells damaged by chemotherapeutic agents or radiation. That is, the composition for promoting the self-renewal of hematopoietic stem cells of the present invention may be used for the treatment of any disease that requires hematopoietic stem cell transplantation, resulting from damage or lack of hematopoietic stem cells, or other diseases.

In addition, the composition for promoting the self-renewal of neuronal stem cells of the present invention may be used for the treatment of patients in need of transplant, who suffer from neurodegenerative diseases selected from the group consisting of stroke, Alzheimer's disease, Parkinson's disease, Huntington's disease, Amyotrophic lateral sclerosis (ALS), Pick's disease, Niemann pick disease, and spinal cord injury disease.

In accordance with another aspect, the present invention relates to a method for promoting the self-renewal of adult stem cells by co-culturing adult stem cells with the mesenchymal stromal cells.

In particular, the present invention relates to a method for promoting the self-renewal of adult stem cells, comprising the steps of: co-culturing adult stem cells with the β-catenin or notch ligand-overexpressed mesenchymal stromal cells; and transplanting the co-cultured adult stem cells in vivo. In addition, the present invention relates to a method for promoting the self-renewal of adult stem cells, comprising the steps of preparing the β-catenin or notch ligand-overexpressed mesenchymal stromal cells; and transplanting the prepared mesenchymal stromal cells in vivo.

Figure 1:
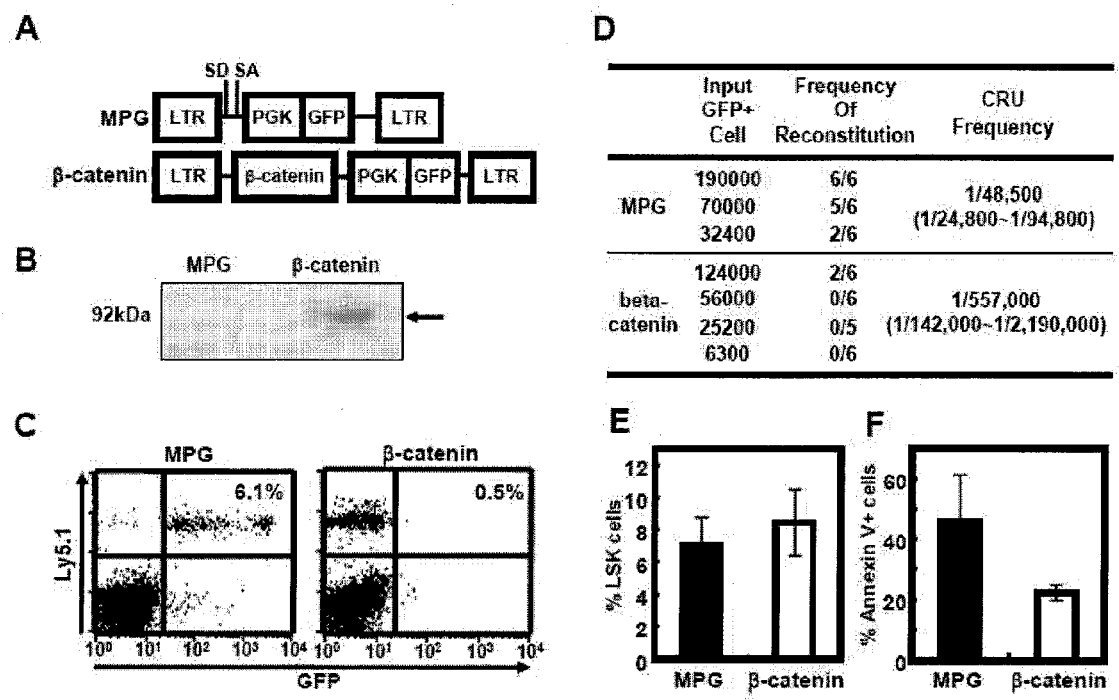
In FIG. 1, (A) shows the structures of a retroviral vector (MPG) and a retroviral vector (MPG-β-catenin) expressing a stable form of β-catenin, (B) shows the accumulation of the stable form of β-catenin in stromal cells after retroviral transduction of 5-FU BMCs with the retroviral vector (MPG or MPG-β-catenin)

In one specific embodiment of the present invention, the present inventors observed that the effect of directly expressing the stable form of β-catenin after retroviral transduction of hematopoietic stem cells was the loss of hematopoietic stem cells; this loss was not accompanied by the increase in the LSK cells or apoptotic cells (FIG. 1). However, when hematopoietic stem cells were co-cultured with mesenchymal stromal cells that were transduced with a retroviral vector expressing a stable form of β-catenin, CRU frequency of hematopoietic stem cells was increased, and significantly higher levels of repopulation were displayed in vivo reconstitution. Of note, the results suggest that physical contact between hematopoietic stem cells and β-catenin-activated stroma cells caused enhanced maintenance and expansion of hematopoietic stem cells (FIGS. 2 and 3), which is supported by compartmentalization of Wnt/β-catenin signal molecules in the hematopoietic microenvironment. In this regard, analysis of the gene expression patterns of Wnt signaling molecules revealed that canonical Wnt receptors were predominantly compartmentalized on stromal cells rather than hematopoietic stem cells. In particular, a subset of genes involved in canonical Wnt-signal reception, Frizzled receptors, RYK, co-receptors LRP5/6, Dkk-2, or Ror2, was more highly expressed in stromal cells, whereas Wnt ligands or sFRP, Dkk-4 that inhibit the Wnt signaling, were enriched in hematopoietic cells of 5-FU treated BMC (FIG. 4). Moreover, accumulation of the active form of β-catenin was selectively observed in the endosteal stroma of bone marrows in "stimulated" and "stressed" marrows, and not in homeostatic "steady-state" marrows (FIG. 5). Taken together, Wnt signal activation and β-catenin accumulation in bone marrow stroma may function as a crucial microenvironmental cue for HSC self-renewal in the stem cell niche.

The present inventors also examined the down-stream signals in Wnt/β-catenin activated stroma. They found that in β-catenin activated mesenchymal stroma, the notch ligands jagged-1 and dll-1 were induced (FIGS. 6 to 8), and secreted growth factors such as Gas-6 (growth arrest-specific), CXCL5, and proliferin-2 were also induced, and induction of dlk-1 (delta-like 1 homolog) and MAGP-2/MFAP-5 (microfibril-associated glycoprotein2), involved in facilitating shedding of jagged-1 in the cell membrane, were also observed (FIG. 9 and Table 2). The undifferentiated hematopoietic cell population (CD45$^+$Lin$^-$Sca-1$^+$) purified from a co-culture with β-catenin/stroma was examined. Observed were significant induction of the notch down-stream genes Hes-1 and deltex-1 as well as induction of bmi-1, a gene whose expression level is tightly linked to HSC self-renewal. Moreover, after using the γ-secretase inhibitor for inhibition of notch signals, the cultured hematopoietic stem cells were analyzed for LSK (Lin-Sca-1+c-kit+) cells. Expansion of undifferentiated hematopoietic stem cells was found to be abrogated, as compared to the control (DMSO) group. Thus, the results suggest that Wnt/β-catenin activated stromal cells maintain hematopoietic stem cells in an undifferentiated state, and the activation of notch signals is involved in their expansion (FIG. 9C).

Furthermore, the present inventors confirmed that transplantation of the β-catenin activated mesenchymal stromal cells into bone marrows exhibited a 4-fold higher CRU frequency of regenerated BMC, and thus β-catenin stabilized in the stromal microenvironment promotes HSC self-renewal in bone marrows (FIG. 10). They also demonstrated that the β-catenin activated mesenchymal stromal cells could exert analogous effects on the non-hematopoietic stem cells including neuronal stem cells, as well as hematopoietic stem cells (FIG. 11).

In accordance with still another aspect, the present invention relates to β-catenin or notch ligand-overexpressed mesenchymal stromal cells for promoting the self-renewal of adult stem cells.

In the present invention, β-catenin or notch ligands may be overexpressed in mesenchymal stromal cells by using the methods known in the art, and preferably by transducing the mesenchymal stromal cells with a vector expressing β-catenin or notch ligands.

As such, β-catenin or notch ligand-overexpressed mesenchymal stromal cells are co-cultured with adult stem cells, or transplanted into bone marrows, thereby exerting the effect of promoting the self-renewal of adult stem cells.

MODE FOR INVENTION

Hereinafter, the present invention will be described in more detail with reference to Examples. However, these Examples are for illustrative purposes only, and the invention is not intended to be limited by these Examples.

Example 1

Materials and Preparation 1-1. Preparation of Animal

For congenic murine transplantation model, 8 to 12-week-old C57BL/6J-Ly5.2 (BL6) mice and C57BL/6J-Pep3b-Ly5.1 (Pep3b) mice were used as recipients and donors, respectively. Non-obese diabetic severe combined immune deficient mice (NOD/LtSz-scid/scid (NOD/SCID) mice) from Jackson Lab were bred and maintained in HEPA-filtered microisolator cages. Experiments were undertaken with approval from the Animal Experiment Board of the Catholic University of Korea.

1-2. Cell Purification and Culture

Murine bone marrow cells enriched with hematopoietic progenitors were obtained by 4-days-prior i.v. injection of mice with 150 mg/kg body weight of 5-FU (5-fluorouracil, Sigma, St. Louis, Mo.). In addition, for primitive hematopoietic populations, bone marrow cells were first depleted of lineage (CD5, CD45R, CD11b, TER119, Gr-1, 7-4)-positive cells using an immunomagnetic column (Stemsep™, Stemcell Technologies, Vancouver, Ca), and then sorted for LSK (Lin-Sca-1+c-kit+) cells.

Umbilical cord blood cells (UCB) were collected with approval from the Institutional Bioethics Review Board of the Catholic University of Korea. CD34+ cells were isolated and purified from the umbilical cord blood using a CD34 progenitor cell selection system (DynalBiotech, Oslo, Norway) in accordance with the manufacturer's instructions.

In addition, mesenchymal stromal cells (MSCs) were obtained from murine and human bone marrows. Established MSCs were subcultured until all cells become negative for hematopoietic marker CD45.

Example 2

Effect on Hematopoietic Function of β-Catenin Stabilized Directly in HSCs

The present inventors observed that the effect of directly expressing the stable form of β-catenin after retroviral transduction of hematopoietic stem cells was the loss of hematopoietic stem cells; this loss was not accompanied by the increase in the % of LSK cells or apoptotic cells.

In particular, murine hematopoietic stem cells were transduced with a retroviral vector encoding a stable form of β-catenin (S33Y) and a control vector (FIG. 1A), respectively. For the transduction of the retroviral vectors into murine hematopoietic stem cells, 5-FU treated and Lin-(lineage depleted) bone marrow cells (BMC) were pre-stimulated for 48 hrs in the serum-free media containing IMDM and serum substitute (BIT™, StemCell Technologies) supplemented with $10^{-4}$ mol/L 2-mercaptoenthanol (Sigma) plus 40 µg/ml low density lipoprotein (Sigma), and 100 ng/ml murine steel factor (R & D Systems, Minneapolis, Minn.), 100 ng/ml human flt3-ligand (R&D), and 50 ng/ml human thrombopoietin (CytoLab/PeproTech, Rehovot, Israel), and harvested. Then, the cells were cultured in the media containing identical cytokines with virus for about 16 hrs, and this procedure was further repeated twice (total three infections). The transduced cells were transplanted into recipients, and cultured ex-vivo in the media containing the cytokine mixture such as IMDM and 10% fetal bovine serum (FBS).

For Western blot analysis of the stable form of β-catenin, the cells were lysed in a 2× Laemli buffer, and subjected to electrophoresis, followed by immunoblotting using an anti-active-β-catenin antibody (Upstate, N.Y.). The blot was visualized using an ECL™ (Amersham, Buckinghamshire, UK). For Annexin V assay, the transduced GFP+Lin-Sca-1+ cells were incubated in Annexin V-FITC (BD Pharmingen) for 30 min, and then stained with propidium iodide (PI: 1 mg/ml) for flow cytometric analysis (FacsCaliber™, BD Bioscience, San Jose, Calif., USA). Isotype control antibodies were used to set the control gate excluding 99.9% of PI(−) cells.

As a result, gene transfer efficiency into 5-FU murine BMCs reached 70 to 80%, as determined by the percent of GFP (+) cells on 2 days after transduction. Accumulation of the stable form of β-catenin protein was detected only in cells transduced with β-catenin (FIG. 1B). In addition, when β-catenin transduced cells were transplanted into lethally irradiated recipients at serial dilution doses, levels of donor-derived transduced (GFP+) cells were dramatically decreased in cells transduced with β-catenin, as compared to the levels of GFP+ cells in recipients of equivalent numbers of control transduced (MIG) cells (FIGS. 1C,D). This decrease corresponded to an 11-fold lower frequency of CRUs for the β-catenin transduced cells compared to the control transduced cells at the time of transplant (1/557,000 vs. 1/48,500 for β-catenin and control transduced). In this regard, there was no observed difference in apoptotic cells as determined by Annexin V binding to the undifferentiated fraction (Lin-Sca-1+) in β-catenin transduced cells compared to control transduced cells (FIG. 1F), showing no effect on cell survival. Furthermore, this loss was not accompanied by the increase in the % of LSK cells that had been observed when β-catenin was stabilized in vivo (FIG. 1E).

Taken together, it can be seen that the primary effect of β-catenin stabilization is the loss rather than the expansion of hematopoietic stem cells.

Example 3

Effect of β-Catenin Stabilization in Stromal Cells on the Hematopoietic Activity of Co-Cultured HSCs 3-1. Effect on Self-Renewal of Murine HSCs In vitro The present inventors observed that hematopoietic reconstitution was enhanced when hematopoietic stem cells were co-cultured with the β-catenin stabilized stromal cells, whereas the direct stabilization of β-catenin by retroviral transduction of hematopoietic stem cells resulted in a dramatic decrease in CRU.

In particular, for preparation of mesenchymal stromal cells secreting β-catenin, the stable form of the β-catenin gene (S33Y) was cloned into the retroviral vector expressing GFP under the PGK (phosphoglycerate kinase) promoter (MSCV-PGK-GFP, MPG), and retroviral particles were produced by cotransfection of 293 T cells with each retroviral vector plus plasmids containing gag-pol, VSV-G (vesicular stomatitis virus glycoprotein) and GALV (gibbon ape leukemia virus) envelope. Then, supernatants were concentrated, and used to infect GPE-86 cells or mesenchymal stromal cells. For the preparation of mesenchymal stromal cells expressing the stable form of β-catenin, each of murine and human mesenchymal stromal cells were infected with MPG or MPG-β-catenin three times, followed by sorting for transduced (GFP+) cells. The mesenchymal stromal cells were found to be Sca-1 positive and non-hematopoietic (CD45−) cells, and exhibited no hematopoietic activity after transplantation into irradiated mice.

The possibility of autonomous action of cytokines on 5-FU BMCs was minimized by co-culturing with stroma for 5 days. Evaluated by limiting-dilution transplantation, it revealed a 3.5-fold higher number of CRUs in the co-cultured group with stromal cells expressing the stable form of β-catenin than the control group (<1/96000 vs 1/28000 for control vs co-cultured group). However, the enhancing effect was not seen when HSCs were co-cultured with stroma separated by a trans-well filter, suggesting that the effect was dependent on physical contact between HSCs and β-catenin activated stroma (FIG. 3B).

3-2. Effect on Self-Renewal Of Murine HSCs In vivo

To further examine the enhancing effect of β-catenin-activated stroma, 5-FU BMCs from donor mice (Pep3b, Ly5.1) were intravenously injected into irradiated (900 rad) recipient mice (BL6, Ly5.2) along with $1\times10^5$ helper cells derived from recipient origin. Repopulation of transplanted cells in the recipients was assessed by flow cytometry to measure the proportion of leukocytes expressing donor-origin (Ly5.1) surface antigen in their blood or bone marrows. Lineages of repopulated hematopoietic cells were analyzed by staining with anti-Mac-1 (BD Pharmingen, San Diego, Calif.) and anti-Gr-1 antibodies (BD Pharmigen) for myeloid cells and with anti-B220 antibody (BD Pharmingen) for lymphoid engraftment.

As shown in FIG. 2C, transplants from the β-catenin/stroma co-culture displayed significantly higher levels of repopulation than those from the control group (MPG), from 3 to 24 weeks post-transplantation ($p<0.05$). The enhanced repopulation was not associated, however, with significant alteration in lympho-myeloid differentiation of reconstituted, donor-derived cells.

For characterization of reconstituted cells, the primary recipient bone marrow was transplanted into secondary recipients, resulting in an 18-fold higher number of CRU frequency in marrows that had received cells co-cultured on β-catenin/stroma than in marrows receiving cells on control stroma (1155 CRUs vs. 65 CRUs: co-culture vs. control) (FIG. 3A) during in-vivo reconstitution. In addition, a difference in CRUs was gradually increased compared to those determined immediately after the co-culture (3.5-fold), indicating that hematopoietic stem cells in contact with β-catenin-activated stroma are maintained in an undifferentiated state for self-renewal.

3-3. Effect on Self-Renewal Of Human HSCs In vivo

To compare the effect of β-catenin on human hematopoietic stem cells, human mesenchymal stromal cells were prepared as described above, and used as feeder cells for co-culture with CD34+ cells from human umbilical cord blood. CD34+ cells co-cultured on the mesenchymal stromal cells were transplanted into lethally irradiated (300 cGy) NOD/SCID mice along with $1\times10^5$ helper cells at serial dilution doses. NOD/SCID mice were provided with acidified drinking water supplemented with 100 mg/L ciprofloxacin (Bayer AG, Leverkusen, Germany). Their bone marrow cells were incubated with anti-human CD45-PE antibody (BD Pharmingen), anti-human CD71-PE antibody (BD Pharmingen), anti-human CD19, 20 antibody (BD Pharmingen) or anti-human CD13, 15 (BD Pharmingen) to analyze human cell engraftment by flow cytometry. Antibodies were used in 5% human serum with 2.4G2 (an antimouse Fc receptor antibody). The levels of lymphoid and myeloid engraftment in the recipient mice blood were determined after 16 weeks. Recipient mice with 1%, or more, of donor-lymphoid and myeloid engraftments were scored as positive. 1 CRU (competitive repopulation unit) was defined as the cell dose that resulted in negative engraftment (failure) in 37% of the test mice. CRU frequencies and 95% CI (confidence interval) were calculated by applying Poisson statistics to the proportion of negative mice using L-Calc software (StemCell Technologies).

As a result, the β-catenin/stroma group showed higher repopulation than the control group (18% vs 5.6%), and high frequency of lymphoid-myeloid reconstitution was observed at a limiting-dose (5/6 co-culture group vs 2/6 control group) (FIG. 3D), suggesting that human hematopoietic stem cells are also similarly regulated by stroma-mediated Wnt signaling.

Example 4

Immunostaining and RT-PCR

In order to examine physiological correlation of the above results, the present inventors examined the gene expression patterns of Wnt signaling molecules in the stromal and hematopoietic compartments of bone marrow. That is, they hypothesized that the stromal microenvironment serves as a primary target site of Wnt/β-catenin signals, and examined the expression of Wnt signaling molecules including Wnt ligands, receptors, and co-receptors in the hematopoietic microenvironment.

For immunohistochemistry of the bone marrows, femurs of non-irradiated and irradiated (900 rad) mice in a paraffin block (5-μm) were de-paraffinized and the antigen retrieved with proteinase-K treatment for 5 min. The endogenous peroxidase was blocked with 0.3% hydrogen peroxide for 5 min. The slides were then incubated with an anti-activated β-catenin antibody overnight at 4° C., washed and incubated with a secondary antibody (HRP) for 30 min at room temperature and visualized with DAKO REAL™ enVision™ Detection System DAKO, Glostrup, Denmark), followed by hematoxylin counterstaining and observation with Olympus BX-50 microscope (Uplan-1).

To examine the expression pattern of Wnt-related genes, total RNAs were purified from BMCs and MSCs sorted for CD45(−), and subjected to RT-PCR analysis.

As shown in FIG. 4, receptors for Wnt/β-catenin signals (Frz1, 2, 7, 8) were predominantly enriched in stromal cells rather than in hematopoietic cells, whereas Wnt ligands (Wnt1, Wnt2b, Wnt4, and Wnt10b) that activate β-catenin signaling were predominantly expressed in the hematopoietic compartment. In contrast, Wnt 5a, a non-canonical Wnt ligand related to the inhibition of canonical pathways, was enriched in stromal cells and the receptors Frizzled 4, 6 that are involved in non-canonical protein kinase-C activation were enriched in 5-FU BMCs. These results reveal that the distribution of Wnt/β-catenin signaling molecules is anatomically compartmentalized, and the expression patterns between the canonical and non-canonical Wnt signals exhibit reciprocal proportion in the hematopoietic microenvironment. Dkk-2, a molecule that binds to LRP6 and activates canonical Wnt signaling, or Ror-2, an orphan receptor tyrosine kinase that potentiates canonical pathway signaling were also enriched in stromal cells, whereas Dickkopf4 or secreted frizzled-related proteins (SFR1, 2), which inhibit the signaling, were enriched in 5-FU BMCs compared to stromal cells.

Taken together, the expression patterns of signaling molecules suggested that a primary target of Wnt activation is the stromal cells rather than hematopoietic stem cells in the bone marrow microenvironment, and hematopoietic cells provide Wnt ligands. In this regard, the present inventors examined whether β-catenin activation occurs in a compartmentalized fashion in the bone marrow microenvironment in conditions associated with stimulating HSC self-renewal. The stable β-catenin (unphosphorylated form) accumulation was observed in the trabecular region of bone marrows where most long-term hematopoietic stem cells reside and their self-renewal occurs. Consistent with the expression patterns in FIG. 5, the β-catenin accumulation was selectively observed in the endosteal stroma of bone marrows in "stressed" (by radiation) marrows, and not in "steady-state" marrows, indicating that Wnt-activated stroma plays a key role for HSC self-renewal in the stem cell niche.

Example 5

Induction of Notch Ligands in β-Catenin Activated Stromal Cells

The observed effects of β-catenin activated mesenchymal stromal cells on HSCs in the specific conditions associated with stimulating HSCs suggested that a cross-talk may occur between stroma and HSCs. Thus, the present inventors explored the downstream effect of Wnt/β-catenin activated stromal cells. In the present invention, the following primer sets were used for RT-PCR or real time-PCR.

INDUSTRIAL APPLICABILITY

The composition comprising β-catenin or notch ligand-overexpressed mesenchymal stromal cells of the present invention is used to promote the maintenance of an undifferentiated state and the self-renewal of adult stem cells without additional cell regulatory factors.

The invention claimed is:

1. A method for promoting the self-renewal of hematopoietic stem cells, comprising the steps of:
   co-culturing the hematopoietic stem cells with β-catenin-overexpressing mesenchymal stromal cells into which a gene encoding β-catenin is transfected;
   transplanting the co-cultured hematopoietic stem cells into an irradiated mammal; and
   allowing the transplanted hematopoietic stem cells to engraft, thereby promoting the self-renewal of hematopoietic stem cells.

2. A method for promoting the self-renewal of hematopoietic stem cells, comprising the steps of:
   preparing β-catenin-overexpressing mesenchymal stromal cells by transfection of a gene encoding β-catenin;
   transplanting the prepared mesenchymal stromal cells into the bone marrow of an irradiated mammal; and
   allowing the transplanted mesenchymal stromal cells to engraft, thereby promoting the self-renewal of hematopoietic stem cells in the bone marrow.

3. The method according to claim 1, wherein the β-catenin is a stable form of β-catenin.

4. The method according to claim 1, wherein the mesenchymal stromal cells are transduced with a vector containing a gene encoding β-catenin.

5. A method for promoting the self-renewal of neuronal stem cells, comprising the steps of:
   co-culturing the neuronal stem cells with β-catenin-overexpressing mesenchymal stromal cells in the presence of bFGF (basic fibroblast growth factor), wherein the mesenchymal stromal cells are transduced with a vector containing a gene encoding β-catenin;

transplanting the co-cultured neuronal stem cells into an irradiated mammal; and allowing the transplanted neuronal stem cells to engraft, thereby promoting the self-renewal of neuronal stem cells.

6. The method according to claim 5, wherein the β-catenin is a stable form of β-catenin.

* * * * *